United States Patent [19]

Kay et al.

[11] Patent Number: 5,693,844
[45] Date of Patent: Dec. 2, 1997

[54] 2-CYANO-3-HYDROXY-PROPENAMIDES

[75] Inventors: David Paul Kay; Elizabeth Anne Kuo, both of Swindon; Richard Alexander Williamson, Hitchin, all of England

[73] Assignee: Roussel UCLAF, France

[21] Appl. No.: 721,500

[22] Filed: Sep. 26, 1996

[30] Foreign Application Priority Data

Oct. 2, 1995 [GB] United Kingdom ............... 9520092

[51] Int. Cl.⁶ .............................................. C07C 255/12
[52] U.S. Cl. .............................................. 558/392
[58] Field of Search .............................................. 558/392

[56] References Cited

U.S. PATENT DOCUMENTS

| | | | |
|---|---|---|---|
| 4,285,863 | 8/1981 | Battisti et al. | 260/176 |
| 4,335,256 | 6/1982 | De Witt et al. | 562/450 |
| 4,710,514 | 12/1987 | Takahashi et al. | 514/485 |
| 4,946,867 | 8/1990 | Manabe et al. | 514/521 |

*Primary Examiner*—Johann Richter
*Assistant Examiner*—Ebenezer Sackey
*Attorney, Agent, or Firm*—Bierman, Musserlian and Lucas LLP

[57] ABSTRACT

A compound selected from the group consisting of a compound of the formula

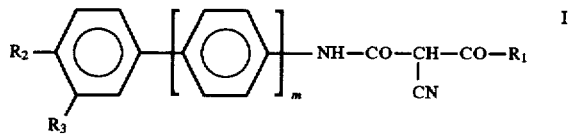

wherein $R_1$ is cyclopropyl or $-CH_2-CH=CH_2$, $R_2$ is $-S(O)_n-(CF_2)_x-CF_3$, n is 1 or 2, x is 0 or 1, $R_3$ is hydrogen or alkyl of 1 to 3 carbon atoms, m is 0 or 1 and its non-toxic, pharmaceutically acceptable addition salts with a base having anti-inflammatory activity.

17 Claims, No Drawings

2-CYANO-3-HYDROXY-PROPENAMIDES

STATE OF THE ART

EP applications No. 484,223, No. 533,573, No. 551,230 and No. 606,175 and German application Serial No. 2,555,789 describe various compounds having a 2-cyano-3-hydroxy-propenamide structure different from the compounds of the invention and which lack the unexpected potency of the inventive compounds on the relevant human enzymes.

OBJECTS OF THE INVENTION

It is an object of the invention to provide the novel compounds of formula I and their pharmaceutical addition salts and a process and intermediates for their preparation.

It is another object of the invention to provide novel anti-inflammatory compositions and a novel method of treating inflammation in warm-blooded animals, including humans.

These and other objects and advantages of the invention will become obvious from the following detailed description.

THE INVENTION

The novel compounds of the invention are selected from the group consisting of a compound of the formula

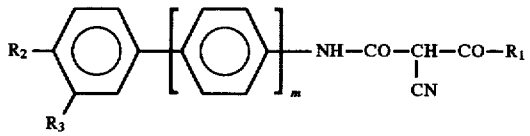

wherein $R_1$ is cyclopropyl or $-CH_2-CH=CH_2$, $R_2$ is $-S(O)_n-(CF_2)_x-CF_3$, n is 1 or 2, x is 0 or 1, $R_3$ is hydrogen or alkyl of 1 to 3 carbon atoms, m is 0 or 1 and its non-toxic, pharmaceutically acceptable addition salts with a base.

Among the preferred compounds of formula I are those wherein $R_1$ is cyclopropyl, those wherein $R_3$ is hydrogen or methyl, more preferably hydrogen and preferably wherein $R_3$ is hydrogen or methyl, $R_2$ is $-S(O)_n-(CF_2)_x-CF_3$, $R^1$ is cyclopropyl, m is zero, n is 1 or 2 and x is zero.

Specific preferred compounds of the invention are selected from the group consisting of N-(4'-trifluoromethylsulfinyl-phenyl)-2-cyano-3-cyclopropyl-3-hydroxy-prop-2-enamide and N-(4'-trifluoromethylsulfinyl-phenyl)-2-cyano-3-cyclopropyl-3-hydroxy-prop-2-enamide and their non-toxic, pharmaceutically acceptable salts with a base.

The compounds of formula I are acidic in nature and will form salts with a non-toxic, pharmaceutically acceptable base by reaction with about stoichiometric amounts thereof with or without the isolation of the acidic compound of formula I.

The process of the invention for the preparation of a compound of formula I comprises reacting a compound of the formula

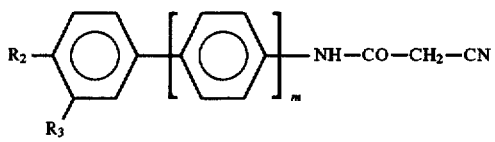

wherein $R_2$, $R_3$, m, n and x are as defined above, successively with a base optionally in the presence of a catalyst; then with a compound of the formula

wherein X is a leaving group and $R_1$ is as defined above. Preferably, the base is sodium hydroxide or lithium diisopropylamide and the catalyst is imidazole. A preferred leaving group is halogen.

The compounds of formula IV may, for example, be prepared by the oxidation at the sulfur atom of a compound of the formula

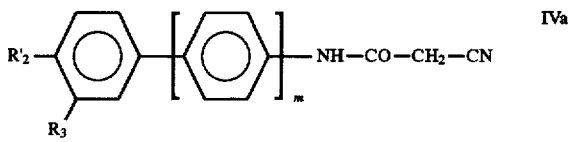

wherein $R'_2$ is $-S-(CF_2)_x-CF_3$ and $R_3$, x and m are as defined above.

The compounds of formula IVa may, for example, be prepared by the reaction of a compound of the formula

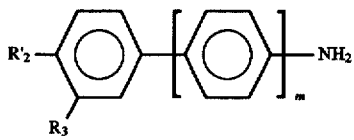

wherein $R'_2$, x, $R_3$ and m are as defined above, with a compound of the formula

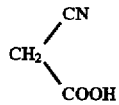

or a functional derivative thereof.

Compounds of formula IV may also be prepared by first oxidizing the sulfur atom of compounds of formula IIa (as defined above) followed by reaction of the product with a compound of formula III as defined above or a derivative thereof.

Preferably, the reaction of the compounds of formula IIa and III is effected in the presence of diisopropylcarbodiimide or dicyclohexylcarbodiimide in an anhydrous organic solvent such as dichloromethane or tetrahydrofuran. The functional derivative of the acid of formula III is preferably cyanoacetyl chloride prepared in situ from phosphorous pentachloride and cyanoacetic acid (see J. Med. Chem., 1985, Vol 28, p. 559–568). The oxidation of compounds of formula IVa can be carried out by using known oxidation agents such as peracetic acid. Depending on the reaction conditions e.g. temperature, solvent, reaction time, the trifluoromethylthio group can be oxidized to the sulfinyl- or sulfonyl- group.

The reaction of the compound of formula IV with sodium hydride is preferably effected in an anhydrous organic solvent such as tetrahydrofuran. The reaction with a compound of formula V is also preferably effected in an anhydrous organic solvent such as tetrahydrofuran.

Compounds of the Formula

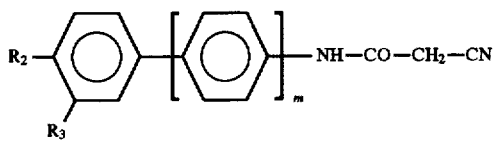

wherein $R_2$ is $—S(O)_n—(CF_2)_x—CF_3$, n is 1 or 2 and x is zero or 1; $R_3$ is hydrogen or alkyl of 1 to 3 carbon atoms; and m is zero or 1 are new compounds and constitute a further feature of the invention.

The novel anti-inflammatory compositions of the invention are comprised of an anti-inflammatorily effective amount of a compound of formula I or its addition salt with a non-toxic, pharmaceutically acceptable base and an inert pharmaceutical carrier. The compositions may be in the form of tablets, dragees, capsules, gelatin capsules, granules, suppositories and injectable solutions or suspensions.

Examples of suitable carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions of the invention possess very interesting pharmacological properties. Of particular note is their remarkable anti-inflammatory activity. They inhibit both the inflammatory response caused by irritant agents, and delayed hypersensitivity reactions, by hindering activation of the immune cells by a specific antigen. They are useful in the treatment of rheumatoid arthritis, chronic inflammatory diseases of immune or non-immune origin (e.g. graft-versus-host disease, transplantation reactions, uveitis) and cancer.

The immunosuppressive effects of the new compounds can for example be demonstrated by the dihydroorotate dehydrogenase enzyme assay. Dihydroorotate dehydrogenase (DHO-DH) catalyzes the fourth step in de novo pyrimidine biosynthesis. Its inhibition would lead to pyrimidine nucleotide depletion and consequently inhibition of DNA and RNA synthesis and cell proliferation. Pyrimidines are also required for glycosylation of lipids and proteins. Cell proliferation is a critical component of the immune response, during which the immune cells have a high nucleotide requirement. A DHO-DH inhibitor would thus be a potential immunosuppressive agent and in addition would have therapeutic benefits in disorders involving aberrant cell proliferation.

The novel method of treating inflammatory conditions such as rheumatoid arthritis, chronic inflammatory diseases of immune or non-immune origin or cancer in warm-blooded animals, including humans, comprises administering to warm-blooded animals an anti-inflammatorily effective amount of a compound of formula I or its salt with a base. The, compounds may be administered orally, rectally or parenterally and the usual daily dosage is 0.0013 to 2.66 mg/kg depending on the condition treated, the specific compound and the method of administration.

In the following examples, there are described several preferred embodiments to illustrate the invention. However, it should be understood that the invention is not intended to be limited to the specific embodiments.

EXAMPLE 1

Preparation of N-(4'-trifluoromethylsulfinyl-phenyl)-cyanoacetamide and of N-(4'-trifluoromethylsulfonyl-phenyl)-cyanoacetamide.

A. 4.35 g (0.0167 mole—produced in EP Patent No. 0,484,223) of N-(4'-trifluoromethylthio-phenyl)-cyanoacetamide in 15 ml of acetic acid were stirred overnight at room temperature with 8.0 ml of 32% w/v (0.035 mole) of peracetic acid and the mixture was poured into an ice/water mixture. The mixture was extracted with ethyl acetate and the organic phase was washed with aqueous sodium bicarbonate, dried over $MgSO_4$ and evaporated to dryness to obtain 4.6 g of a colorless solid which was chromatographed on silica gel (1 to 10% acetone in dichloromethane) to obtain 2.7 g (59% yield) of N-(4'-trifluoromethylsulfinyl-phenyl)-cyanoacetamide as colorless crystals melting at 164° to 165° C.

IR (Kbr) 3280, 1678, 1615, 1592, 1550, 1497, 1405, 1348, 1307, 1262, 1195, 1175, 1141, 1085, 1067;

$^1$H NMR ($D_6$-DMSO) δ 10.80 (1H, brs), 7.91 (4H, s), 4.03 (2H, s). This product can be used without further purification.

B. The combined 1.7 g of the residual fractions from the chromography were dissolved in 6 ml of acetic acid and treated with 6 g of peracetic acid. The mixture was heated at 50° C. overnight and was then poured into water and extracted with ethyl acetate. The organic phase was washed with aqueous sodium bicarbonate, dried over $MgSO_4$ and evaporated to dryness. The 100 g of residue were chromatographed on silica gel (2–3% acetone in dichloromethane) to obtain 1.06 g (22% yield) of N-(4'-trifluoromethylsulfonyl-phenyl)-cyanoacetamide in the form of colorless crystals melting at 135° to 137° C.

IR (KBr) 3343, 3316, 1724, 1608, 1592, 1538, 1409, 1351, 1217, 1199, 1186, 1170, 1147, 1075;

$^1$H NMR ($D_6$-DMSO) δ 11.09 (1H,s), 8.15 (2H, d, J=9), 4.08 (2H,s). This product can be used without further purification.

EXAMPLE 2

N-(4'-trifluoromethylsulfinyl-phenyl)-2-cyano-3-cyclopropyl-3-hydroxy-prop-2-enamide.

3.1 g (0.0112 mole) of N-(4'-trifluoromethylsulfinyl-phenyl)-cyanoacetamide in 100 ml of anhydrous THF and 10 mg of catalytic imidazole and 0.75 g (0.0246 mole) of sodium hydride (80% oil dispersion) were stirred at room temperature for 90 minutes and then 1.32 ml (0.0146 mole) of cyclopropylcarbonyl chloride were added dropwise. The solution was stirred at room temperature for 10 minutes, was poured into a 1M HCl/water mixture and was filtered. The product was dissolved in dichloromethane and chromatographed on a short silica column (dichloromethane) to obtain 2.54 g (66% yield) of N-(4'-trifluoromethylsulfinyl-phenyl)-2-cyano-3-cyclopropyl-3-hydroxy-prop-2-enamide melting at 155°–157° C.

IR (KBr) 3280, 2219, 1603, 1575, 1536, 1496, 1406, 1353, 1195, 1174, 1141, 1090, 1070, 895;

$^1$H NMR ($CDCl_3$) δ 15.49 (1H, s), 7.89 (1H, s), 7.82 (4H, s), 2.18 (1H,m), 1.37 (2H, m), 1.22 (2H, m).

Analysis: $C_{14}H_{11}F_3N_2O_3S$. Calcd: % C, 48.84; % H 3.22; % N, 8.13; % F 16.55; % S, 9.31. Found: C, 49.03; H, 3.29; N, 8.17; F, 16.39; S. 9.35.

EXAMPLE 3

N-(4'-trifluoromethylsulfonyl-phenyl)-2-cyano-3-cyclopropyl-3-hydroxy-prop-2-enamide.

Using the procedure of Example 2, N-(4'-trifluoromethylsulfonyl-phenyl)-cyano acetate was reacted to obtain a 65% yield of the desired product melting at 168°–170° C.

IR (KBr) 3300, 2218, 1638, 1529, 1499, 1411, 1363, 1349, 1322, 1268, 1247, 1216, 1190, 1177, 1142, 1079, 986, 894, 841;

$^1$H NMR (CDCl$_3$) δ 15.30 (1H, s), 8.03 (2H, d, J=8.8), 7.92 (1H, s), 7.85 (2H, d, J=8.8), 2.18 (1H, m), 1.41 (2H, m), 1.25 (2H, m).

Analysis: C$_{14}$H$_{11}$F$_3$N$_2$O$_4$S. Calcd: % C, 46.67; % H 3.08; % F, 15.82; % N, 7.77; % S, 8.90. Found: C, 47.01; H, 3.17; F, 15.57; N, 7.84; S, 8.79.

EXAMPLE 4

Dihydroorotate Dehydrogenase (DHO-DH) Assay

Human spleen membrane DHO-DH catalyzed conversion of dihydroorotate to orotate is accompanied by reduction of coenzyme Q$_{10}$. Reoxidation of coenzyme Q$_{10}$ is linked to reduction of dichlorophenolindophenol and is monitored as a loss of absorbance at 650 nm. The rate of loss in absorbance is a direct measurement of the rate of the DHO-DH enzyme catalyzed reaction. Reaction rates were measured in the presence of a range of concentrations of test compound and the concentration giving 50% inhibition (IC$_{50}$) was determined graphically (see Williamson et al. (1995), "Dihydroorotate dehydrogenase, a high affinity binding protein for A77 1726 and mediator of a range of the biological effects of the immunomodulatory compounds", The Journal of Biological Chemistry).

Preparation of Human Spleen Membranes

Crude membrane preparations were made using a modification of a published differential centrifugation procedure. All procedures were carried out on ice or at a temperature of 4° C. using pre-cooled buffers and equipment.

The spleen tissue was chopped and then homogenized with a teflon glass homogenizer (about 10 passes at 250 rpm) in 10 volumes of a homogenization buffer (10 mM Tris-HCl containing 0.25M sucrose, 10 μg/ml soybean trypsin inhibitor, 2 μg/ml aprotinin, pepstatin A and leupeptin pH 7.4). The homogenate was centrifuged at ⁻470 g for 10 minutes and the supernatant was saved. Pellets were resuspended in 4–6 volumes of homogenization buffer using 5 passes of the teflon glass homogenizer (250 rpm) and centrifuged for 10 minutes at ⁻470 g. The supernatant was combined with that from the first centrifugation step (post nuclear fraction) and the pellets containing nuclei and tissue debris were discarded. The post nuclear supernatant was centrifuged at 125,000 g for 40 minutes. The pellets were resuspended in homogenization buffer (2 ml/g wet tissue) using about 10 passes of the teflon glass homogenizer. Aliquots of the preparation were stored at –80° C. Membranes were not refrozen once thawed (see Ozols J. "Preparation of Membrane Fractions", in: Methods in Enzymology Volume 182, Guide to Protein Purification (Ed. Deutscher MP), pp. 225–235. Academic Press, London, 1990).

Inhibition of human spleen dihyroorotate dehydrogenase activity by five test compounds was assessed using a DCIP-linked assay (see Lakaschus et al (1992) Biochem. Pharmacol; Vol. 43, pp. 1025–1030). Membranes (0.33–0.5 mg protein) were incubated with 100 μM coenzyme Q$_{10}$ in 50 mM Tris-HCl, 0.1% Triton X-100, 1 mM KCN pH 8.0. Following a 90 minute preincubation at 37° C., the reaction was initiated by addition of 500 μM of dihydroorotate and the reduction of DCIP (200 μM) was monitored by loss of absorbance at 650 nm using a 96-well plate reader at 37° C. Drug concentrations increased in half log unit or full log unit intervals with each concentration tested at least in triplicate.

Results

The following results were found for three prior art compounds (A, B, C) and for compounds of examples 3 and 2 in the human DHO-DH enzyme inhibition test:

| Structure | Compounds | IC$_{50}$ (nM) |
|---|---|---|
| CN—⟨Ph⟩—NH—CO—CH(CN)—CO—◁ | A | 1950–2100 |
| CF$_3$—⟨Ph⟩—NH—CO—CH(CN)—CO—C≡CH | B | >100,000 |
| CF$_3$—⟨Ph⟩—NH—CO—CH(CN)—CO—CH=C(CH$_3$) | C | 79,400 |
| CF$_3$—SO$_2$—⟨Ph⟩—NH—CO—CH(CN)—CO—◁ | Ex. 3 | 68 |
| CF$_3$—SO—⟨Ph⟩—NH—CO—CH(CN)—CO—◁ | Ex. 2 | 300 |

Various modifications of the products and processes of the invention may be made without departing from the spirit or scope thereof and it is to be understood that the invention is intended to be limited only as defined in the appended claims.

What is claimed is:

1. A compound selected from the group consisting of a compound of the formula

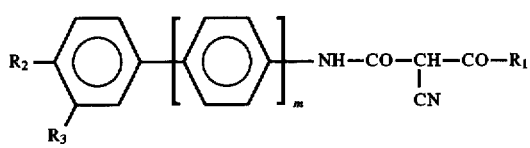

wherein $R_1$ is cyclopropyl or —$CH_2$—$CH=CH_2$, $R_2$ is —$S(O)_n$—$(CF_2)_x$—$CF_3$, n is 1 or 2, x is or 1, $R_3$ is hydrogen or alkyl of 1 to 3 carbon atoms, m is 0 or 1 and its non-toxic, pharmaceutically acceptable addition salts with a base.

2. A compound of claim 1 wherein $R_3$ is cyclopropyl.

3. A compound of claim 1 wherein $R_3$ is hydrogen or methyl.

4. A compound of claim 1 selected from the group consisting of N-(4'-trifluoromethylsulfinyl-phenyl)-2-cyano-3-cyclopropyl-3-hydroxyl-prop-2-enamide and N-(4'-trifluoromethylsulfinyl-phenyl)-2-cyano-3-cyclopropyl-3-hydroxy-prop-2-enamide.

5. A compound of claim 2 wherein $R_3$ is hydrogen or methyl.

6. A process for the preparation of a compound of claim 1 comprising reacting a compound of the formula

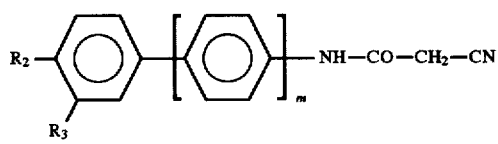

wherein $R_2$ is —$S(O)_o$—$(CF_2)_x$—$CF_3$, n is 1 or 2, x is 1, $R_3$ is hydrogen or alkyl of 1 to 3 carbon atoms, m is 0 or 1, successively with a base optionally in the presence of a catalyst; then with a compound of the formula

wherein X is a leaving group and $R_1$ is cyclopropyl or —$CH_2$—$CH=CH_2$.

7. The process of claim 6 wherein the catalyst is imidazole and the leaving group is halogen.

8. The process of claim 6 wherein the compound of formula IV is obtained by oxidation of the sulfur atom of a compound of the formula

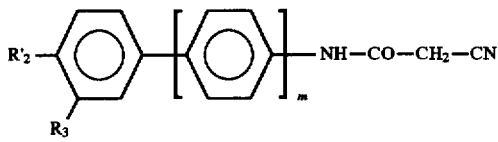

wherein $R'_2$ is —S—$(CF_2)X$—$CF_3$, x is 1, $R_3$ is hydrogen or alkyl of 1 to 3 carbon atoms, m is 0 or 1.

9. The process of claim 8 wherein the compound of formula IVa is obtained by reacting a compound of the formula

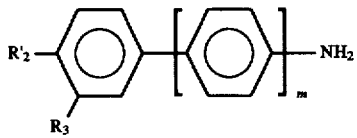

in which $R'_2$ x is 1, $R_3$ is hydrogen or alkyl of 1 to 3 carbon atoms, m is 0 or 1, with a compound of the formula

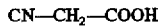

or an acid halide thereof.

10. The process of claim 6 wherein the compound of formula IV is obtained by oxidizing the sulfur atom of a compound of the formula

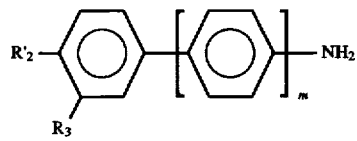

then reacting the latter with a compound of the formula

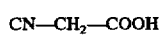

or an acid halide thereof.

11. A compound of the formula

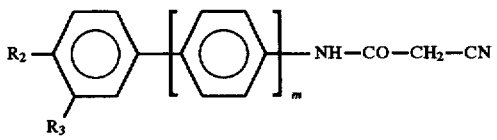

wherein $R_2$ is —$S(O)_n$—$(CF_2)_x$—$CF_3$, n is 1 or 2, X is zero or 1, $R_3$ is hydrogen or alkyl of 1 to 3 carbon atoms and m is zero or 1.

12. An anti-inflammatory composition comprising an anti-inflammatorily effective amount of a compound of claim 1 and an inert pharmaceutical carrier.

13. A method relieving inflammation in warm-blooded animals comprising administering to warm-blooded animals an anti-inflammatory effective amount of a compound of claim 1.

14. The method of claim 13 wherein $R_1$ is cyclopropyl.

15. The method of claim 13 wherein $R_3$ is hydrogen or methyl.

16. The method of claim 14 wherein $R_3$ is hydrogen or methyl.

17. The method of claim 13 wherein the compound is selected from the group consisting of N-(4'-trifluoromethylsulfinyl-phenyl)-2-cyano-3-cyclopropyl-3-hydroxyl-prop-2-enamide and N-(4'-trifluoromethylsulfinyl-phenyl)-2-cyano-3-cyclopropyl-3-hydroxy-prop-2-enamide.

* * * * *